United States Patent
Bernhardt

(10) Patent No.: US 8,825,361 B1
(45) Date of Patent: Sep. 2, 2014

(54) METHODS AND SYSTEMS FOR DETERMINING PERFORMANCE CHARACTERISTICS OF MECHANICAL SYSTEMS BASED ON FUEL PROPERTIES

(75) Inventor: Roger Bernhardt, O'Fallon, MO (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 13/269,861

(22) Filed: Oct. 10, 2011

(51) Int. Cl.
*G06F 19/00* (2011.01)
*G01N 31/00* (2006.01)
*B65B 1/30* (2006.01)

(52) U.S. Cl.
USPC ................. 701/123; 702/22; 141/94

(58) Field of Classification Search
CPC .................... G06K 19/06037; G06K 19/0614; G06K 7/12; G06K 19/06009; G06K 19/14; G06K 2019/06225; G06K 2019/06234; G06K 9/00577; G09F 3/00; G09F 3/0294; G01N 21/643; G01N 21/6489; G01N 19/06009; G01N 1/28; B82Y 15/00; B82Y 30/00
USPC ........ 701/96–115, 538, 123; 702/22, 32, 104, 702/109, 116; 700/241; 141/9, 94, 104, 141/105, 107, 234, 285, 301, 302
See application file for complete search history.

(56) References Cited

U.S. PATENT DOCUMENTS

| | | | | |
|---|---|---|---|---|
| 5,261,270 A | * | 11/1993 | Gonze et al. | 73/61.43 |
| 5,814,830 A | * | 9/1998 | Crowne | 250/577 |
| 7,811,520 B2 | | 10/2010 | Bernhardt | |
| 2006/0269804 A1 | * | 11/2006 | Nakamura et al. | 429/22 |
| 2011/0093187 A1 | * | 4/2011 | Skaff et al. | 701/123 |
| 2012/0205449 A1 | * | 8/2012 | Lewis et al. | 235/468 |

FOREIGN PATENT DOCUMENTS

WO    WO-01/37207    *    5/2001

OTHER PUBLICATIONS

Unknown, "InkSure's Taggant Technology for Fuel Security and Energy Protection", Aug. 15, 2011, 1 page, Inksure Technologies.

* cited by examiner

*Primary Examiner* — Muhammad Shafi
(74) *Attorney, Agent, or Firm* — Armstrong Teasdale LLP

(57) ABSTRACT

Methods and systems for use in determining one or more performance characteristics of a mechanical system that includes a combustion engine. One or more values of a physical property of fuel are associated with a performance characteristic (e.g., an operating characteristic and/or a maintenance characteristic) of a mechanical system to create a fuel-performance relationship. An actual value of the physical property of a fuel to be burned by the combustion engine is determined using one or more sensors. A predicted value of the performance characteristic is determined based on the actual value of the physical property and the fuel-performance relationship.

20 Claims, 5 Drawing Sheets

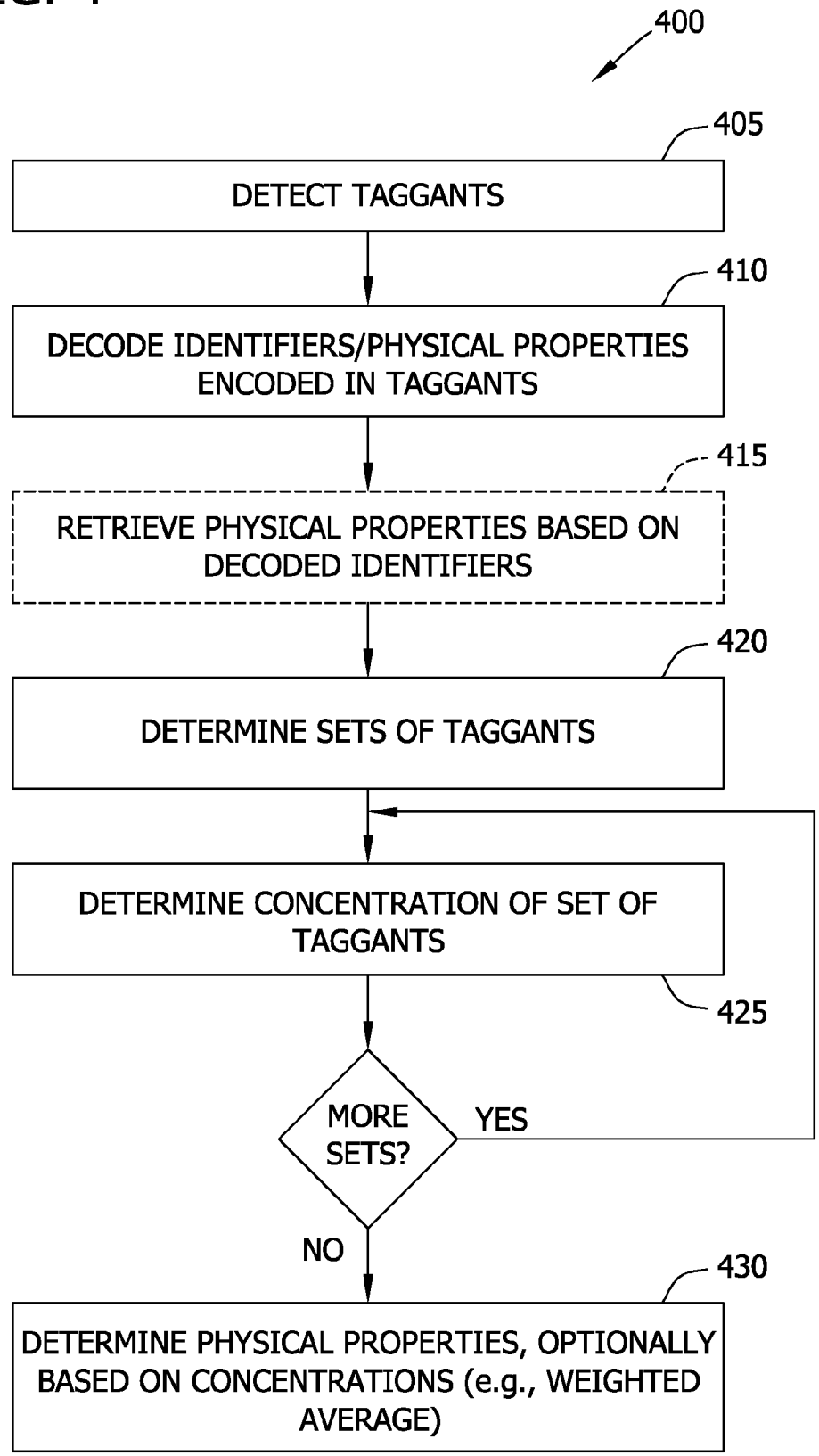

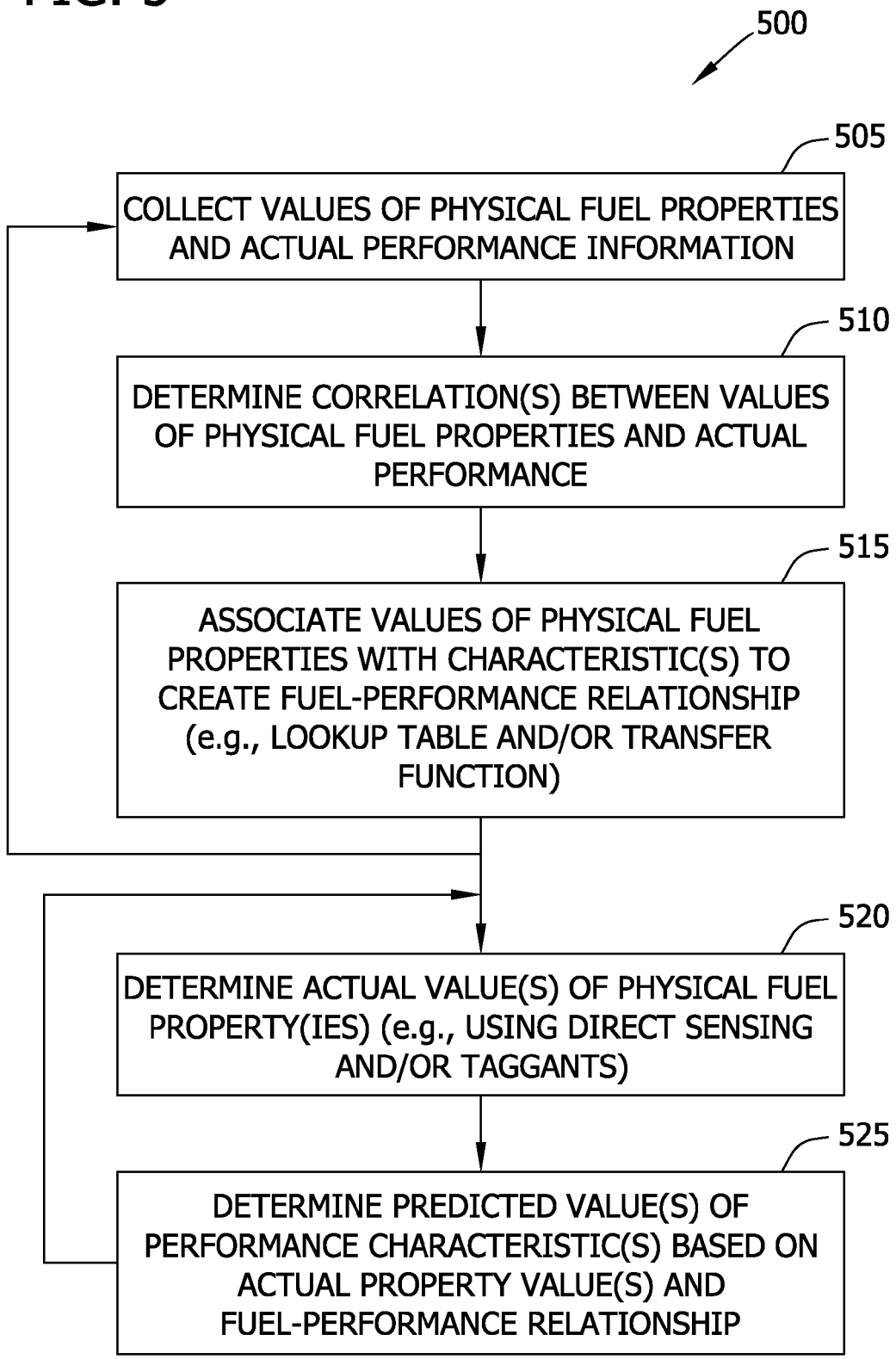

METHODS AND SYSTEMS FOR DETERMINING PERFORMANCE CHARACTERISTICS OF MECHANICAL SYSTEMS BASED ON FUEL PROPERTIES

BACKGROUND

The field of the disclosure relates generally to fuel properties and, more specifically, to methods and systems for use in predicting system performance characteristics based on physical fuel properties.

Fuels that are used in combustion engines may exhibit different properties, such as energy density, stability, and lubricity. Such varying properties may affect the performance of a combustion engine as well as that of a system (e.g., a vehicle or an electrical generator) that includes a combustion engine. For example, lubricity may affect mechanical wear of engine components, and energy density may affect vehicle range. The properties of the fuel used in a combustion engine may be used to speculate about the performance (e.g., operating and/or maintenance characteristics) of the engine. However, at least some known fuel systems do not allow an operator to determine such properties.

Moreover, within a supply chain between the fuel manufacturer and the fuel user, fuels may be blended, and contaminants may be introduced. Accordingly, determining fuel properties based on information provided by the manufacturer(s) may be infeasible and/or impossible.

BRIEF DESCRIPTION

In one aspect, a system is provided for use in determining one or more performance characteristics of a mechanical system that includes a combustion engine. The system includes a memory for storing a fuel-performance relationship that associates one or more values of a physical property of fuel with a performance characteristic of a mechanical system. The performance characteristic includes an operating characteristic and/or a maintenance characteristic. The system also includes a sensor configured to produce a signal representing a physical fuel property and/or an identifier of a fuel. The system further includes a processor that is coupled to the memory and to the sensor. The processor is programmed to determine an actual value of a physical property of fuel based on the signal produced by the sensor, and to determine a predicted value of the performance characteristic based on the actual value of the physical property and the fuel-performance relationship.

In another aspect, a method is provided for use in determining one or more performance characteristics of a mechanical system that includes a combustion engine. The method includes associating one or more values of a physical property of fuel with a performance characteristic of a mechanical system to create a fuel-performance relationship. The performance characteristic includes an operating characteristic and/or a maintenance characteristic. An actual value of the physical property of a fuel to be burned by the combustion engine is determined using one or more sensors in the mechanical system. A predicted value of the performance characteristic is determined based on the actual value of the physical property and the fuel-performance relationship.

In yet another aspect, one or more non-transitory computer-readable media having computer-executable components embodied thereon are provided. The computer-executable components include a property determination component and a performance prediction component. When executed by at least one processor unit, the property determination component causes the processor unit to determine an actual value of a physical property of fuel based on a signal produced by a sensor. When executed by at least one processor unit, the performance prediction component causes the processor unit to associate one or more values of a physical property of fuel with a performance characteristic of a mechanical system to create a fuel-performance relationship. The performance characteristic includes an operating characteristic and/or a maintenance characteristic. The performance prediction component also causes the processor unit to determine a predicted value of the performance characteristic based on the actual value of the physical property and the fuel-performance relationship.

The features, functions, and advantages that have been discussed can be achieved independently in various embodiments or may be combined in yet other embodiments further details of which can be seen with reference to the following description and drawings.

BRIEF DESCRIPTION OF THE DRAWINGS

FIG. 4 is a flowchart of an exemplary method for use in determining fuel properties using the system shown in FIG. 2.

FIG. 5 is a flowchart of an exemplary method for use in determining one or more performance characteristics of a mechanical system that includes a combustion engine using the system shown in FIG. 2.

DETAILED DESCRIPTION

Embodiments described herein facilitate indicating and determining one or more physical properties of a fuel to be used with a combustion engine, such that the performance (e.g., operating and/or maintenance characteristics) of the engine and/or of a system including the engine may be predicted. Further, such a determination of physical properties and/or such a prediction of performance may be accomplished when multiple fuels have been blended, and even when multiple blended fuels have been blended into a "blend of blends."

Physical fuel properties may be directly detected and/or indicated by taggants added to the fuel. As used herein, taggants include chemical and/or physical markers that indicate information, such as an identifier associated with a fuel and/or a physical fuel property. In exemplary embodiments, taggants have a size large enough to enable detection but small enough to avoid negatively affecting the operation of a combustion engine burning the fuel.

Physical properties may be directly detected and/or measured by specialized sensors. For example, a conductivity sensor may measure the conductivity of a fuel. Taggants may be detected using a taggant sensor that corresponds to the form of taggant used. For example, information may be encoded in an optically scannable taggant and subsequently scanned by an optical sensor. As another example, information may be encoded as a chemical signature in a chemical taggant and subsequently detected using a spectroscopic sensor. Such examples are provided for illustrative purposes only, and it is contemplated that the embodiments described herein are operable with any taggants and corresponding sensors.

Figure 1:
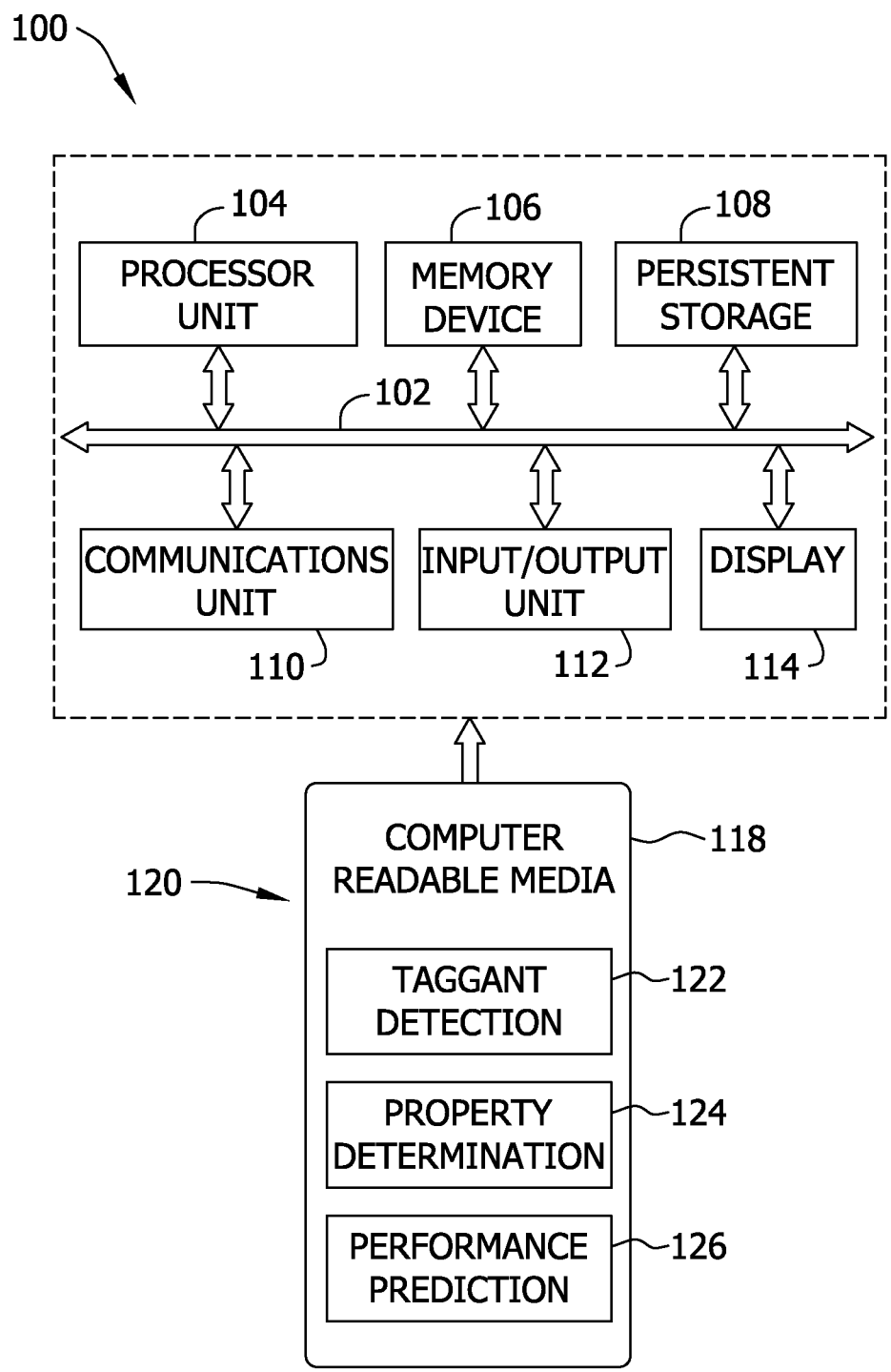
FIG. 1 is a block diagram of an exemplary computing device.

FIG. 1 is a block diagram of an exemplary computing device 100. In the exemplary embodiment, computing device 100 includes communications fabric 102 that provides communications between a processor unit 104, a memory 106, persistent storage 108, a communications unit 110, an input/output (I/O) unit 112, and a presentation interface, such as a display 114. In addition to, or in alternative to, the presentation interface may include an audio device (not shown) and/or any device capable of conveying information to a user.

Processor unit 104 executes instructions for software that may be loaded into memory 106. Processor unit 104 may be a set of one or more processors or may include multiple processor cores, depending on the particular implementation. Further, processor unit 104 may be implemented using one or more heterogeneous processor systems in which a main processor is present with secondary processors on a single chip. In another embodiment, processor unit 104 may be a homogeneous processor system containing multiple processors of the same type.

Memory 106 and persistent storage 108 are examples of storage devices. As used herein, a storage device is any piece of hardware that is capable of storing information either on a temporary basis and/or a permanent basis. Memory 106 may be, for example, without limitation, a random access memory and/or any other suitable volatile or non-volatile storage device. Persistent storage 108 may take various forms depending on the particular implementation, and persistent storage 108 may contain one or more components or devices. For example, persistent storage 108 may be a hard drive, a flash memory, a rewritable optical disk, a rewritable magnetic tape, and/or some combination of the above. The media used by persistent storage 108 also may be removable. For example, without limitation, a removable hard drive may be used for persistent storage 108.

A storage device, such as memory 106 and/or persistent storage 108, may be configured to store data for use with the processes described herein. For example, a storage device may store computer-executable instructions, executable software components (e.g., taggant detection components and/or property determination components), detected taggant information, fuel properties, fuel identifiers, fuel-performance relationships, and/or any other information suitable for use with the methods described herein.

Communications unit 110, in these examples, provides for communications with other computing devices or systems. In the exemplary embodiment, communications unit 110 is a network interface card. Communications unit 110 may provide communications through the use of either or both physical and wireless communication links.

Input/output unit 112 enables input and output of data with other devices that may be connected to computing device 100. For example, without limitation, input/output unit 112 may provide a connection for user input through a user input device, such as a keyboard and/or a mouse. Further, input/output unit 112 may send output to a printer. Display 114 provides a mechanism to display information, such as any information described herein, to a user. For example, a presentation interface such as display 114 may display a graphical user interface, such as those described herein.

Instructions for the operating system and applications or programs are located on persistent storage 108. These instructions may be loaded into memory 106 for execution by processor unit 104. The processes of the different embodiments may be performed by processor unit 104 using computer implemented instructions and/or computer-executable instructions, which may be located in a memory, such as memory 106. These instructions are referred to herein as program code (e.g., object code and/or source code) that may be read and executed by a processor in processor unit 104. The program code in the different embodiments may be embodied on different physical or tangible computer-readable media, such as memory 106 or persistent storage 108.

Program code 116 is located in a functional form on non-transitory computer-readable media 118 that is selectively removable and may be loaded onto or transferred to computing device 100 for execution by processor unit 104. Program code 116 and computer-readable media 118 form computer program product 120 in these examples. In one example, computer-readable media 118 may be in a tangible form, such as, for example, an optical or magnetic disc that is inserted or placed into a drive or other device that is part of persistent storage 108 for transfer onto a storage device, such as a hard drive that is part of persistent storage 108. In a tangible form, computer-readable media 118 also may take the form of a persistent storage, such as a hard drive, a thumb drive, or a flash memory that is connected to computing device 100. The tangible form of computer-readable media 118 is also referred to as computer recordable storage media. In some instances, computer-readable media 118 may not be removable.

Alternatively, program code 116 may be transferred to computing device 100 from computer-readable media 118 through a communications link to communications unit 110 and/or through a connection to input/output unit 112. The communications link and/or the connection may be physical or wireless in the illustrative examples. The computer-readable media also may take the form of non-tangible media, such as communications links or wireless transmissions containing the program code.

In some illustrative embodiments, program code 116 may be downloaded over a network to persistent storage 108 from another computing device or computer system for use within computing device 100. For instance, program code stored in a computer-readable storage medium in a server computing device may be downloaded over a network from the server to computing device 100. The computing device providing program code 116 may be a server computer, a workstation, a client computer, or some other device capable of storing and transmitting program code 116.

Program code 116 may be organized into computer-executable components that are functionally related. For example, program code 116 may include one or more taggant detection components 122, property determination components 124, performance prediction components 126, and/or any component suitable for practicing the methods described herein. Each component may include computer-executable instructions that, when executed by processor unit 104, cause processor unit 104 to perform one or more of the operations described herein. In exemplary embodiments, taggant detection component 122 causes processor unit 104 to detect one or more taggants in a fuel. Property determination component 124 causes processor unit 104 to determine a value of a physical property of a fuel based on the detected taggants, and to determine a concentration of the taggants in the fuel. Performance prediction component 126 causes processor unit 104 to associate one or more values of a physical property of fuel with a performance characteristic (e.g., an operating characteristic and/or a maintenance characteristic) of a mechanical system to create a fuel-performance relationship, and to determine a predicted value of the performance characteristic based on an actual value of the physical property and the fuel-performance relationship.

The different components illustrated herein for computing device 100 are not meant to provide architectural limitations to the manner in which different embodiments may be implemented. The different illustrative embodiments may be implemented in a computer system including components in addition to or in place of those illustrated for computing device 100. For example, other components shown in FIG. 1 can be varied from the illustrative examples shown.

As one example, a storage device in computing device 100 is any hardware apparatus that may store data. Memory 106, persistent storage 108 and computer-readable media 118 are examples of storage devices in a tangible form.

In another example, a bus system may be used to implement communications fabric 102 and may include one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, without limitation, memory 106 or a cache such as that found in an interface and memory controller hub that may be present in communications fabric 102.

Figure 2:
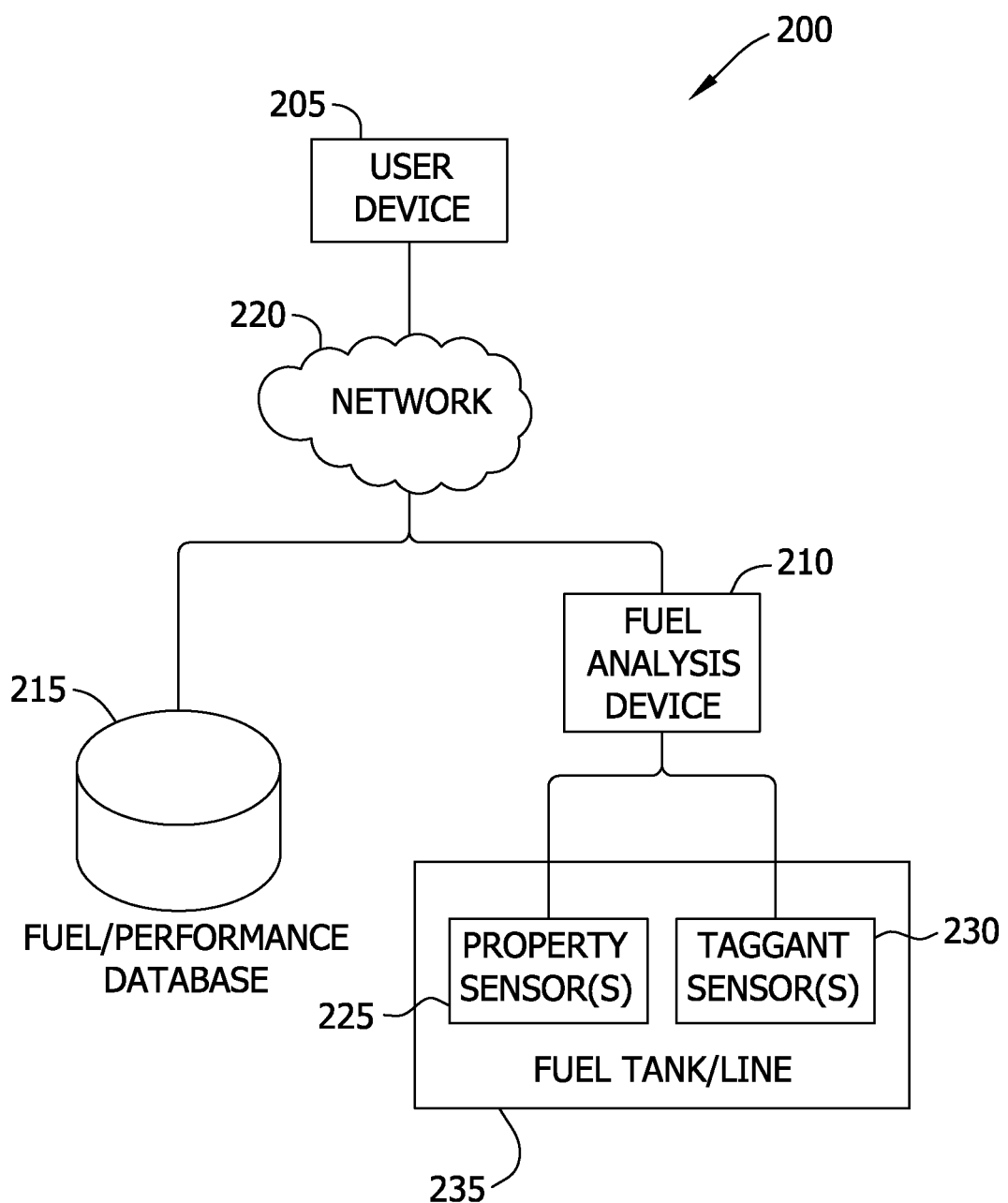
FIG. 2 is a block diagram illustrating an exemplary system for use in indicating and/or determining fuel properties.

FIG. 2 is a block diagram illustrating an exemplary system 200 for use in indicating and/or determining fuel properties. System 200 includes a user device 205, a fuel analysis device 210, and a fuel/performance database 215 coupled in communication by a network 220. In exemplary embodiments, each of user device 205, fuel analysis device 210, and fuel/performance database 215 is an instance of a computing device 100. Network 220 may include, for example, a local area network (LAN), a wireless LAN, a wide area network (WAN), a mobile telecommunications network, and/or the Internet.

Fuel analysis device 210 is coupled to one or more property sensors 225 and/or one or more taggant sensors 230, which are positioned at least partially within a fuel tank and/or line 235. For example, fuel analysis device 210 may be positioned in a fuel production and/or distribution facility, in which case property sensors 225 and/or taggant sensors 230 may be positioned at least partially within a fuel tank 235 of a fueling system at the facility. As another example, fuel analysis device 210 may be positioned onboard a vehicle, in which case property sensors 225 and/or taggant sensors 230 may be positioned at least partially within a fuel tank and/or fuel line 235 of the vehicle.

Property sensors 225 are configured to directly detect and/or measure one or more physical properties of fuel within fuel tank and/or line 235, and to transmit a signal indicating the physical fuel property(ies) to fuel analysis device 210. Taggant sensors 230 are configured to detect information indicated by taggants within the fuel, and to transmit a signal indicating such information to fuel analysis device 210.

In exemplary embodiments, a property sensor 225 is a sensor configured to directly detect and/or measure a physical property of the fuel. As an example, a conductivity sensor may include two electrodes that extend into fuel contained within fuel tank and/or line 235, and a measuring device for measuring the conductance between the two electrodes. Such a conductivity sensor may be configured to produce a signal indicating the measured conductance. Similarly, property sensors 225 may include any sensor that is operable to detect a physical property of a fuel within fuel tank and/or line 235.

A taggant sensor 230 is a device configured to detect the presence of one or more taggants (e.g., chemical and/or physical markers) within the fuel contained in fuel tank and/or line 235. Taggant sensor 230 corresponds to the form of taggant used. For example, an optical taggant sensor 230 may be used to detect optically scannable taggants, whereas a spectroscopic taggant sensor 230 may be used to detect chemical taggants.

Figure 3:
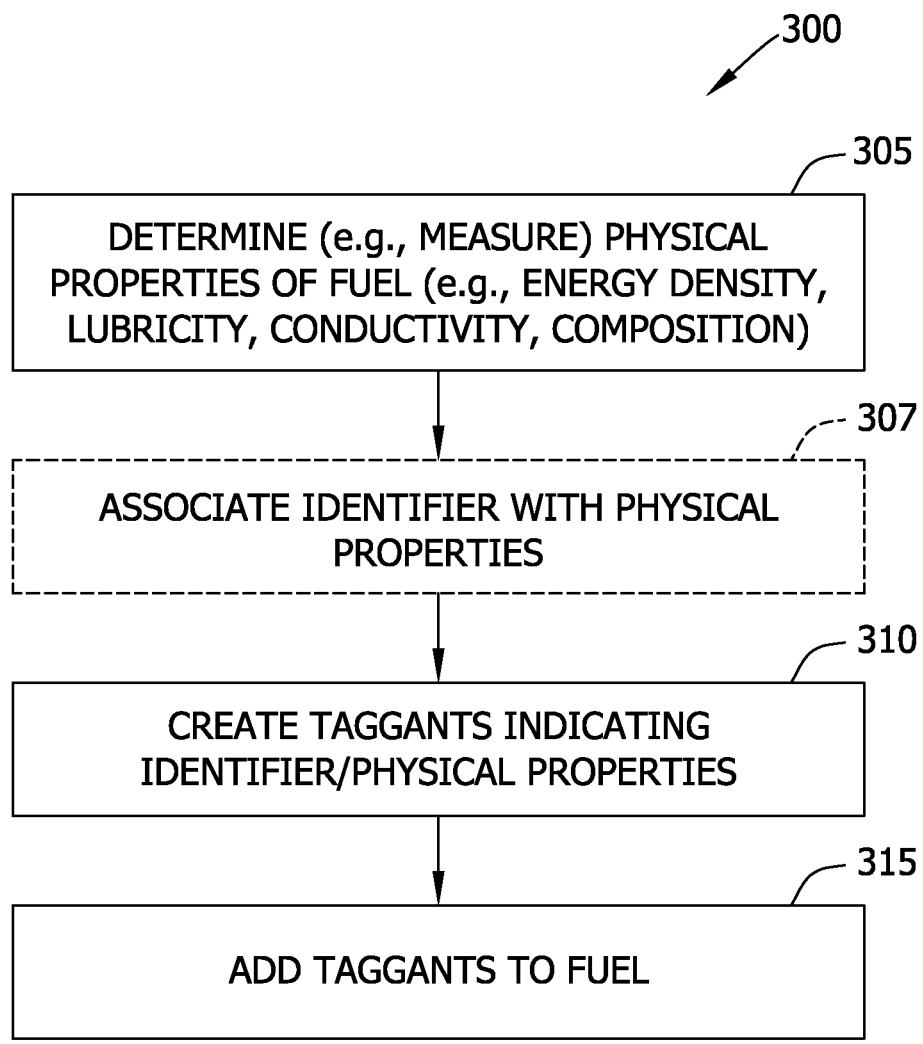
FIG. 3 is a flowchart of an exemplary method for use in indicating fuel properties using the system shown in FIG. 2.

FIG. 3 is a flowchart of an exemplary method 300 for use in indicating fuel properties using system 200 (shown in FIG. 2). Referring to FIGS. 2 and 3, in exemplary embodiments, one or more physical properties of a fuel are determined 305. The physical properties may include, for example, fuel type (e.g., gasoline, ethanol, and/or diesel), composition (e.g., ingredients), energy density, stability, lubricity, acidity, heat capacity, viscosity, conductivity, and/or dielectric constant. Physical fuel properties may be determined 305 in a variety of ways, such as by directly measuring the properties and/or by predicting the properties based on the production process and/or ingredients used to create the fuel. For example, a particular fuel formulation may be known (e.g., based on past measurement and/or experimentation) to result in a particular energy density.

Taggants enabling the subsequent determination of the physical fuel property(ies) are created 310. In exemplary embodiments, a computing device 100 (shown in FIG. 1), such as user device 205 and/or fuel analysis device 210, associated 307 an identifier of the fuel (e.g., a batch number and/or other serial number) with the physical fuel properties that have been determined 305. For example, the identifier and the properties may be associated 307 by storing the identifier and properties in association in fuel/performance database 215. In such embodiments, the taggants created 310 indicate the identifier of the fuel. For example, the fuel identifier may be encoded in the taggants.

In other embodiments, rather than linking physical fuel properties to an identifier, taggants indicating the physical fuel properties themselves are created 310. For example, the physical fuel properties may be encoded in the taggants.

The taggants are added 315 to the fuel. In exemplary embodiments, taggants are added 315 to the fuel substantially at (e.g., within 1%, 2%, or 5% of) a predetermined concentration. Adding the taggants at a known concentration facilitates subsequently determining the amount (e.g., concentration) of a particular fuel in a fuel tank and/or line 235 when multiple fuels are blended together.

FIG. 4 is a flowchart of an exemplary method for use in determining fuel properties using system 200 (shown in FIG. 2). Referring to FIGS. 2 and 4, fuel analysis device 210 detects 405 one or more taggants in the fuel within fuel tank and/or line 235, such as by receiving signals from taggant sensors 230. As described above, the taggants indicate one or more fuel identifiers and/or physical fuel properties.

Fuel analysis device 210 decodes 410 information encoded in the taggants and determines 430 one or more physical properties of the fuel based on the decoded information. In exemplary embodiments, fuel analysis device 210 determines 430 physical fuel properties at least in part by decoding 410 an identifier encoded in the taggants and retrieving 415 a physical fuel property from fuel/performance database 215 based on the decoded identifier. For example, fuel analysis device 210 may retrieve from fuel/performance database all physical properties that are associated with the fuel identifier. In addition, or alternatively, physical fuel properties may be directly encoded in taggants, and fuel analysis device 210 may determine 430 physical fuel properties at least in part by decoding 410 a physical property encoded in a taggant. Accordingly, the physical properties of the fuel in a fuel tank and/or line 235 may be determined 430 based directly on the content of the fuel itself and without reliance on inconvenient and error-prone manual record keeping.

In exemplary embodiments, method 400 facilitates determining 430 fuel properties even when multiple fuels have been blended together. For example, the fuel may include a blend of a first batch of fuel and a second batch of fuel. In such embodiments, fuel analysis device 210 determines 420 how many sets of taggants are present in the fuel. For example, in decoding 410 information encoded in the taggants, fuel analysis device 210 may identify a first set of taggants associated with the first batch of fuel (e.g., indicating a first fuel identifier and/or a first value of a physical fuel property) and a second set of taggants associated with the second batch of fuel (e.g., indicating a second fuel identifier and/or a second value of the same physical fuel property).

Fuel analysis device 210 determines 425 the concentration of each set of taggants in the fuel. For example, fuel analysis device 210 may determine 425 a first concentration of the first set of taggants and a second concentration of the second set of taggants. In exemplary embodiments, the concentration of each set of taggants is equal to the quantity of taggants in the set divided by the total quantity of taggants detected 405. For example, if the first set includes 1000 taggants, and the second set includes 2000 taggants, the concentration of the first set is equal to ⅓ (1000 divided by 3000), and the concentration of the second set is equal to ⅔ (2000 divided by 3000). Alternatively, the concentration of each set of taggants may be equal to the quantity of taggants in the set divided by the expected total quantity of taggants for the volume of fuel in fuel tank and/or line 235. For example, if taggants are added 315 (shown in FIG. 3) to fuels at a predetermined concentration, an expected total quantity of taggants for a volume of fuel may be calculated by multiplying the volume by the predetermined concentration.

When fuel analysis device 210 has determined 425 the concentration of each set of taggants, fuel analysis device 210 determines 430 one or more physical properties of the fuel based at least in part on the concentrations. In exemplary embodiments, fuel analysis device 210 has decoded 410 and/or retrieved 415 numeric values of physical properties corresponding to each set of taggants, as described above. In such embodiments, fuel analysis device 210 may determine 430 the physical properties of the fuel by calculating a weighted average of the decoded/retrieved values, with the values weighted based on the corresponding concentrations. For example, a first value of conductivity (e.g., expressed in siemens per meter) associated with the first set of taggants and a second value of conductivity associated with the second set of taggants may be combined by weighting the first value based on the concentration of the first set of taggants and weighting the second value based on the concentration of the second set of taggants.

Accordingly, exemplary embodiments enable the determination of physical properties of fuel blends and even blends of blends. Such properties are determined in a manner that reflects the proportion of each component fuel in the blend.

In addition to indicating physical fuel properties, embodiments provided herein further facilitate predicting performance of a system in which a fuel is to be combusted. FIG. 5 is a flowchart of an exemplary method 500 for use in determining one or more performance characteristics of a mechanical system that includes a combustion engine using system 200 (shown in FIG. 2).

In exemplary embodiments, values of physical fuel properties and corresponding actual performance information are collected 505 over time. For example, a subset of a fleet of vehicles may be treated as an experimental group for testing a particular fuel. The same fuel may be provided to all vehicles in the experimental group, and resulting performance information may be collected 505. As another example, a fuel may be evaluated in a lab for materials compatibility with one or more components (e.g., a fuel line seal) within a combustion engine and/or mechanical system.

As described herein, collected physical fuel properties may include, without limitation, fuel type (e.g., gasoline, ethanol, and/or diesel), composition (e.g., ingredients), energy density, stability, lubricity, acidity, heat capacity, viscosity, conductivity, and/or dielectric constant. Performance information includes maintenance information and/or operating information. For example, maintenance information may include, without limitation, a system condition at specific times, component replacement events, mechanical wear of one or more components (e.g., per unit of fuel and/or time of exposure), and/or deterioration of one or more components (e.g., per unit of fuel and/or time of exposure). Operating information may include, without limitation, an operating speed (e.g., a maximum operating speed of an engine or mechanical system), an operating range (e.g., with respect to distance and/or meteorological conditions, such as temperature), an engine output per unit of fuel, and/or a mechanical system output per unit of fuel.

In exemplary embodiments, because the relationship between fuel properties and performance characteristics may unpredictable prior to performing method 500, fuel properties and performance information may be over-collected. For example, a relatively large quantity of factors may be sampled, and these factors may be sampled relatively frequently.

Correlations are determined 510 between the values of physical fuel properties and actual performance. For example, determining 510 correlations may include applying regression analysis and/or other statistical methods to the fuel and performance data previously collected 505.

In exemplary embodiments, one or more values of one or more physical fuel properties (e.g., an energy density of the fuel, a stability of the fuel, a lubricity of the fuel, an acidity of the fuel, and/or a heat capacity of the fuel) are associated 515 with a performance characteristic (e.g., an operating characteristic and/or a maintenance characteristic) of a mechanical system based on the determined correlations to create a fuel-performance relationship. For example, fuel-performance relationships may be created for factors demonstrating marked correlation (e.g., a correlation coefficient greater than 0.6) or high correlation (e.g., a correlation coefficient greater than 0.8). As described above, maintenance characteristics include, but are not limited to, mechanical wear per unit of fuel and/or deterioration per unit of fuel. Operating characteristics include, but are not limited to, an operating speed, an operating range, an engine output per unit of fuel, and/or a mechanical system output per unit of fuel.

In some embodiments, creating a fuel-performance relationship includes creating a lookup table that associates a plurality of values of one or more physical properties of fuel with a plurality of values of one or more performance characteristics of the mechanical system. In other embodiments, creating a fuel-performance relationship includes defining a transfer function that relates one or more physical properties of fuel to the performance characteristic of the mechanical system. Fuel-performance relationships may be stored in fuel/performance database 215 and/or distributed to fuel analysis devices 210.

In exemplary embodiments, the collection 505, determination 510, and association 515 described above are performed repeatedly, such that fuel-performance relationships may be refined over time. For example, such repetition may produce a larger data set from which correlations may be determined 510.

In operation, fuel analysis device 210 determines 520, using property sensors 225 and/or taggant sensors 230, an actual value of one or more physical properties of fuel to be burned by a combustion engine (e.g., fuel within fuel tank and/or line 235). As described above, values of physical fuel properties may be determined 520 based on taggants by decoding 410 (shown in FIG. 4) the physical properties directly from the taggants and/or by decoding 410 a fuel identifier and retrieving 415 (shown in FIG. 4) the physical fuel properties from fuel/performance database 215.

Fuel analysis device 210 determines 525 a predicted value of the performance characteristic based on the actual value of the physical property(ies) and the fuel-performance relationship. For example, if the fuel-performance relationship is a lookup table, fuel analysis device 210 determines 525 the predicted value by selecting a value of the performance characteristic from the lookup table based on the actual value(s) of the physical property(ies). If a determined actual value does not appear in the lookup table, fuel analysis device 210 may select the value of the performance characteristic corresponding to a reference value of the physical property that most closely matches the determined actual value. Alternatively, if the determined actual value is between two reference values in the lookup table, fuel analysis device 210 may calculate an average of the values of the performance characteristic corresponding to the two reference values. If the fuel-performance relationship is a transfer function, fuel analysis device 210 may determine 525 the predicted value of the performance characteristic by calculating the value of the performance characteristic based on the transfer function and the actual value of the physical property(ies).

Accordingly, predictions of future performance may be made based on past observed performance and detected fuel properties. Further, such predictions may be repeated over time, and refinement of the fuel-performance relationship enables such predictions to improve in accuracy.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for use in determining one or more performance characteristics of a mechanical system that includes a combustion engine, said system comprising:
    a memory for storing a fuel-performance relationship that associates one or more values of a physical property of fuel with a performance characteristic of a mechanical system, wherein the performance characteristic includes one or more of the following: an operating characteristic and a maintenance characteristic;
    a sensor configured to produce a signal representing one or more of the following: a physical fuel property and an identifier of a fuel; and
    a processor coupled to said memory and said sensor, wherein said processor is programmed to:
        determine an actual value of a physical property of the fuel by decoding one or more codes of one or more taggants within the fuel, based on the signal produced by the sensor; and
        determine a predicted value of the performance characteristic based on the actual value of the physical property and the fuel-performance relationship.

2. A system in accordance with claim 1, wherein said processor is programmed to determine a predicted value of the performance characteristic by determining a predicted value of a maintenance characteristic including one or more of the following: mechanical wear per unit of fuel and deterioration per unit of fuel.

3. A system in accordance with claim 1, wherein said processor is programmed to determine a predicted value of the performance characteristic by determining a predicted value of an operating characteristic including one or more of the following: an operating speed, an operating range, an engine output per unit of fuel, and a mechanical system output per unit of fuel.

4. A system in accordance with claim 1, wherein said memory stores a fuel-performance relationship by storing a lookup table associating a plurality of values of one or more physical properties of fuel with a plurality of values of one or more performance characteristics of the mechanical system, and said processor is programmed to determine the predicted value of the performance characteristic by selecting a value of the performance characteristic from the lookup table based on the actual value of the physical property.

5. A system in accordance with claim 1, wherein said memory stores a fuel-performance relationship by storing a transfer function relating one or more physical properties of fuel to the performance characteristic of the mechanical system, and said processor is programmed to determine the predicted value of the performance characteristic by calculating the value of the performance characteristic based on the transfer function and the actual value of the physical property.

6. A system in accordance with claim 1, wherein said processor is programmed to determine an actual value of the physical property by determining one or more of the following: an energy density of the fuel, a stability of the fuel, a lubricity of the fuel, an acidity of the fuel, and a heat capacity of the fuel.

7. A system in accordance with claim 1, wherein said sensor is further configured to:
    detect an identifier that is encoded in the one or more taggants within the fuel; and
    produce a signal representing the detected identifier,
    wherein said processor is programmed to determine an actual value of the physical property of the fuel by retrieving a physical property from a database based on the detected identifier.

8. A method for use in determining one or more performance characteristics of a mechanical system that includes a combustion engine, said method being implemented by a computing device including a processor coupled to a memory, said method comprising:
    associating, by the computing device, one or more values of a physical property of fuel with a performance characteristic of a mechanical system to create a fuel-performance relationship, wherein the performance characteristic includes one or more of the following: an operating characteristic and a maintenance characteristic;
    determining, by the computing device, using one or more sensors in the mechanical system, an actual value of the physical property of a fuel to be burned by the combustion engine by decoding one or more codes of one or more taggants within the fuel; and determining, by the computing device, a predicted value of the performance characteristic based on the actual value of the physical property and the fuel-performance relationship.

9. A method in accordance with claim 8, wherein determining the predicted value of the performance characteristic comprises determining a predicted value of a maintenance characteristic including one or more of the following: mechanical wear per unit of fuel and deterioration per unit of fuel.

10. A method in accordance with claim 8, wherein determining the predicted value of the performance characteristic comprises determining a predicted value of an operating characteristic including one or more of the following: an operating speed, an operating range, an engine output per unit of fuel, and a mechanical system output per unit of fuel.

11. A method in accordance with claim 8, wherein creating a fuel-performance relationship comprises creating a lookup table associating a plurality of values of one or more physical properties of fuel with a plurality of values of one or more performance characteristics of the mechanical system.

12. A method in accordance with claim 8, wherein creating a fuel-performance relationship comprises defining a transfer function relating one or more physical properties of fuel to the performance characteristic of the mechanical system.

13. A method in accordance with claim 8, wherein determining an actual value of the physical property comprises determining one or more of the following: an energy density of the fuel, a stability of the fuel, a lubricity of the fuel, an acidity of the fuel, and a heat capacity of the fuel.

14. A method in accordance with claim 8, wherein determining an actual value of the physical property comprises determining an actual value of the physical property by scanning the one or more taggants within the fuel using at least one of an optical sensor and a spectroscopic sensor.

15. A method in accordance with claim 8, wherein determining an actual value of the physical property further comprises:

decoding an identifier encoded in the one or more taggants within the fuel; and retrieving a physical property from a database based on the decoded identifier.

16. One or more non-transitory computer-readable media having computer-executable components embodied thereon, said computer-executable components comprising:

a property determination component that when executed by at least one processor unit causes the processor unit to determine an actual value of a physical property of a fuel based on a signal produced by a sensor configured to detect one or more codes of one or more taggants within the fuel; and a performance prediction component that when executed by at least one processor unit causes the processor unit to:

associate one or more values of a physical property of fuel with a performance characteristic of a mechanical system to create a fuel-performance relationship, wherein the performance characteristic includes one or more of the following: an operating characteristic and a maintenance characteristic; and determine a predicted value of the performance characteristic based on the actual value of the physical property and the fuel-performance relationship.

17. One or more non-transitory computer-readable media in accordance with claim 16, wherein said performance prediction component causes the processor to determine a predicted value of the performance characteristic at least in part by determining a predicted value of a maintenance characteristic including one or more of the following: mechanical wear per unit of fuel and deterioration per unit of fuel.

18. One or more non-transitory computer-readable media in accordance with claim 16, wherein said performance prediction component causes the processor to determine a predicted value of the performance characteristic at least in part by determining a predicted value of an operating characteristic including one or more of the following: an operating speed, an operating range, an engine output per unit of fuel, and a mechanical system output per unit of fuel.

19. One or more non-transitory computer-readable media in accordance with claim 16, wherein said performance prediction component creates a fuel-performance relationship at least in part by creating a lookup table associating a plurality of values of one or more physical properties of fuel with a plurality of values of one or more performance characteristics of the mechanical system.

20. One or more non-transitory computer-readable media in accordance with claim 16, wherein said performance prediction component creates a fuel-performance relationship at least in part by creating a transfer function relating one or more physical properties of fuel to the performance characteristic of the mechanical system.

* * * * *